United States Patent
Hoekman et al.

(10) Patent No.: US 11,878,109 B2
(45) Date of Patent: Jan. 23, 2024

(54) SINGLE-USE NASAL DELIVERY DEVICE

(71) Applicant: Impel Pharmaceuticals Inc., Seattle, WA (US)

(72) Inventors: John D. Hoekman, Seattle, WA (US); Albert Kenneth Lavin, Seattle, WA (US); Christopher William Fuller, Seattle, WA (US); Craig Frederick Kohring, Seattle, WA (US)

(73) Assignee: Impel Pharmaceuticals Inc., Seattle, WA (US)

( * ) Notice: Subject to any disclaimer, the term of this patent is extended or adjusted under 35 U.S.C. 154(b) by 799 days.

(21) Appl. No.: 16/875,906

(22) Filed: May 15, 2020

(65) Prior Publication Data

US 2020/0360627 A1 Nov. 19, 2020

Related U.S. Application Data

(60) Provisional application No. 62/849,735, filed on May 17, 2019.

(51) Int. Cl.
  *A61M 11/02* (2006.01)
  *A61M 15/00* (2006.01)

(52) U.S. Cl.
  CPC ........ *A61M 11/02* (2013.01); *A61M 15/0065* (2013.01); *A61M 2210/0618* (2013.01)

(58) Field of Classification Search
  CPC .............. A61M 11/02; A61M 15/0065; A61M 15/0025; A61M 15/08; A61M 2210/0618
  See application file for complete search history.

(56) References Cited

U.S. PATENT DOCUMENTS

| 2,933,259 A | 4/1960 | Raskin |
| 3,425,414 A | 2/1969 | Roche |

(Continued)

FOREIGN PATENT DOCUMENTS

| CN | 104507521 A | 4/2015 |
| CN | 105641787 A | 6/2016 |

(Continued)

OTHER PUBLICATIONS

Appasaheb, et al., "Review on Intranasal Drug Delilvery System", Journal of Advanced Pharmacy Education and Research, vol. 3, Issue 4, Oct. 2013, 14 pages.

(Continued)

*Primary Examiner* — Kendra D Carter
*Assistant Examiner* — Maap Ahmed Ellabib
(74) *Attorney, Agent, or Firm* — Fenwick & West LLP

(57) ABSTRACT

Embodiments relate to a single-use device for delivery of medication into a nasal cavity. In an embodiment, the device includes a propellant canister containing a propellant capable of propelling the compound to the nasal cavity. The propellant canister is displaceable between an unactuated position and an actuated position within the device. The device further includes an actuation element with an actuation lever configured to displace the propellant canister from the unactuated position to the actuated position. The device also includes a puncture element positioned to puncture the propellant canister, which causes the release of the propellant from the propellant canister. The device further includes a dose holding chamber containing a unit dose of the compound. The dose holding chamber is positioned such that propellant flows into the dose holding chamber and causes the compound to be propelled from the dose holding chamber to the nasal cavity of the user.

20 Claims, 11 Drawing Sheets

(56) References Cited

U.S. PATENT DOCUMENTS

| | | |
|---|---|---|
| 3,888,253 A | 6/1975 | Watt et al. |
| 3,906,950 A | 9/1975 | Cocozza |
| 3,908,654 A | 9/1975 | Lhoest et al. |
| 3,971,377 A | 7/1976 | Damani |
| 4,095,596 A | 6/1978 | Grayson |
| 4,187,985 A | 2/1980 | Goth |
| 4,227,522 A | 10/1980 | Carris |
| 4,353,365 A | 10/1982 | Hallworth et al. |
| 4,412,573 A | 11/1983 | Zdeb |
| 4,620,670 A | 11/1986 | Hughes |
| 4,702,415 A | 10/1987 | Hughes |
| 4,896,832 A | 1/1990 | Howlett |
| 4,995,385 A | 2/1991 | Valentini et al. |
| 5,224,471 A | 7/1993 | Marelli et al. |
| 5,307,953 A | 5/1994 | Regan |
| 5,331,954 A | 7/1994 | Rex et al. |
| 5,349,947 A | 9/1994 | Newhouse et al. |
| 5,382,236 A | 1/1995 | Otto et al. |
| 5,398,850 A | 3/1995 | Sancoff et al. |
| 5,435,282 A | 7/1995 | Haber et al. |
| 5,505,193 A | 4/1996 | Ballini et al. |
| 5,516,006 A | 5/1996 | Meshberg |
| 5,711,488 A | 1/1998 | Lund |
| 5,715,811 A | 2/1998 | Ohki et al. |
| 5,797,390 A | 8/1998 | McSoley |
| 5,814,020 A | 9/1998 | Gross |
| 5,819,730 A | 10/1998 | Stone et al. |
| 5,823,183 A | 10/1998 | Casper et al. |
| 5,881,719 A | 3/1999 | Gottenauer et al. |
| 5,901,703 A | 5/1999 | Ohki et al. |
| 5,906,198 A | 5/1999 | Flickinger |
| 5,910,301 A | 6/1999 | Farr et al. |
| 5,954,696 A | 9/1999 | Ryan |
| 6,062,213 A | 5/2000 | Fuisz et al. |
| 6,092,522 A | 7/2000 | Calvert et al. |
| 6,125,844 A * | 10/2000 | Samiotes .......... A61M 15/0065 128/200.23 |
| 6,145,703 A | 11/2000 | Opperman |
| 6,158,676 A | 12/2000 | Hughes |
| 6,180,603 B1 | 1/2001 | Frey |
| 6,186,141 B1 | 2/2001 | Pike et al. |
| 6,189,739 B1 | 2/2001 | von Schuckmann |
| 6,294,153 B1 | 9/2001 | Modi |
| 6,302,101 B1 | 10/2001 | Py |
| 6,313,093 B1 | 11/2001 | Frey |
| 6,347,789 B1 | 2/2002 | Rock |
| 6,367,471 B1 | 4/2002 | Genosar et al. |
| 6,367,473 B1 | 4/2002 | Käfer |
| 6,382,465 B1 | 5/2002 | Perth |
| 6,410,046 B1 | 6/2002 | Lerner |
| 6,491,940 B1 | 12/2002 | Levin |
| 6,540,983 B1 | 4/2003 | Adjei et al. |
| 6,569,463 B2 | 5/2003 | Patel et al. |
| 6,585,172 B2 | 7/2003 | Arghyris |
| 6,585,957 B1 | 7/2003 | Adjei et al. |
| 6,585,958 B1 | 7/2003 | Keller et al. |
| 6,595,202 B2 | 7/2003 | Calvo |
| 6,622,721 B2 | 9/2003 | Vedrine et al. |
| 6,644,305 B2 | 11/2003 | MacRae et al. |
| 6,644,309 B2 | 11/2003 | Casper et al. |
| 6,647,980 B1 | 11/2003 | Gizurarson |
| 6,681,767 B1 | 1/2004 | Patton et al. |
| 6,684,879 B1 | 2/2004 | Coffee et al. |
| 6,701,916 B2 | 3/2004 | Mezzoli |
| 6,715,485 B1 | 4/2004 | Djupesland |
| 6,734,162 B2 | 5/2004 | Van Antwerp et al. |
| 6,810,872 B1 | 11/2004 | Ohki et al. |
| 6,923,988 B2 | 8/2005 | Patel et al. |
| 7,033,598 B2 | 4/2006 | Lerner |
| 7,051,734 B2 | 5/2006 | Casper et al. |
| 7,163,013 B2 | 1/2007 | Harrison |
| 7,182,277 B2 | 2/2007 | Vedrine et al. |
| 7,200,432 B2 | 4/2007 | Lerner et al. |
| 7,214,209 B2 | 5/2007 | Mazzoni |
| 7,231,919 B2 | 6/2007 | Giroux |
| 7,258,119 B2 | 8/2007 | Mazzoni |
| 7,296,566 B2 | 11/2007 | Alchas |
| 7,347,201 B2 | 3/2008 | Djupesland |
| 7,377,901 B2 | 5/2008 | Djupesland et al. |
| 7,476,689 B2 | 1/2009 | Santus et al. |
| 7,481,218 B2 | 1/2009 | Djupesland |
| 7,543,581 B2 | 6/2009 | Djupesland |
| 7,655,619 B2 | 2/2010 | During et al. |
| 7,740,014 B2 | 6/2010 | Djupesland |
| 7,784,460 B2 | 8/2010 | Djupesland et al. |
| 7,799,337 B2 | 9/2010 | Levin |
| 7,832,394 B2 | 11/2010 | Schechter et al. |
| 7,841,337 B2 | 11/2010 | Djupesland |
| 7,841,338 B2 | 11/2010 | Dunne et al. |
| 7,854,227 B2 | 12/2010 | Djupesland |
| 7,866,316 B2 | 1/2011 | Giroux |
| 7,905,229 B2 | 3/2011 | Giroux et al. |
| 7,934,503 B2 | 5/2011 | Djupesland et al. |
| 7,975,690 B2 | 7/2011 | Djupesland |
| 7,994,197 B2 | 8/2011 | Cook et al. |
| 8,001,963 B2 | 8/2011 | Giroux |
| 8,047,202 B2 | 11/2011 | Djupesland |
| 8,119,639 B2 | 2/2012 | Cook et al. |
| 8,122,881 B2 | 2/2012 | Giroux |
| 8,146,589 B2 | 4/2012 | Djupesland |
| 8,171,929 B2 | 5/2012 | Djupesland et al. |
| 8,327,844 B2 | 12/2012 | Djupesland |
| 8,408,427 B2 | 4/2013 | Wong |
| 8,448,637 B2 | 5/2013 | Giroux |
| 8,511,303 B2 | 8/2013 | Djupesland |
| 8,517,026 B2 | 8/2013 | Amon |
| 8,522,778 B2 | 9/2013 | Djupesland |
| 8,550,073 B2 | 10/2013 | Djupesland |
| 8,555,877 B2 | 10/2013 | Djupesland |
| 8,555,878 B2 | 10/2013 | Djupesland |
| 8,596,278 B2 | 12/2013 | Djupesland |
| 8,733,342 B2 | 5/2014 | Giroux et al. |
| 8,757,146 B2 | 6/2014 | Hoekman et al. |
| 8,800,555 B2 | 8/2014 | Djupesland |
| 8,839,790 B2 | 9/2014 | Beck Arnon |
| 8,875,794 B2 | 11/2014 | Carlsen et al. |
| 8,899,229 B2 | 12/2014 | Djupesland et al. |
| 8,899,230 B2 | 12/2014 | Immel |
| 8,910,629 B2 | 12/2014 | Djupesland et al. |
| 8,925,544 B2 | 1/2015 | Flickinger |
| 8,978,647 B2 | 3/2015 | Djupesland et al. |
| 8,987,199 B2 | 3/2015 | Abdel Maksoud et al. |
| 9,010,325 B2 | 4/2015 | Djupesland et al. |
| 9,038,630 B2 | 5/2015 | Djupesland et al. |
| 9,067,034 B2 | 6/2015 | Djupesland et al. |
| 9,072,857 B2 | 7/2015 | Djupesland |
| 9,101,539 B2 | 8/2015 | Nagata et al. |
| 9,119,932 B2 | 9/2015 | Djupesland |
| 9,180,264 B2 | 11/2015 | Young et al. |
| 9,272,104 B2 | 3/2016 | Djupesland |
| 9,446,207 B2 | 9/2016 | Jung |
| 2002/0017294 A1 | 2/2002 | Py |
| 2002/0054856 A1 | 5/2002 | Jones |
| 2002/0056760 A1 | 5/2002 | Piper |
| 2002/0092520 A1 | 7/2002 | Casper et al. |
| 2003/0015191 A1 | 1/2003 | Armstrong et al. |
| 2003/0017119 A1 | 1/2003 | Rabinowitz et al. |
| 2003/0158527 A1 | 8/2003 | Mezzoli |
| 2003/0217748 A1 | 11/2003 | Giroux |
| 2004/0068222 A1 | 4/2004 | Brian |
| 2004/0238574 A1 | 12/2004 | Merk et al. |
| 2005/0023376 A1 | 2/2005 | Anderson |
| 2005/0028812 A1 | 2/2005 | Djupesland |
| 2005/0036985 A1 | 2/2005 | Ensoli |
| 2005/0098172 A1 | 5/2005 | Anderson |
| 2005/0142072 A1 | 6/2005 | Birch et al. |
| 2005/0274378 A1 | 12/2005 | Bonney et al. |
| 2006/0107957 A1 | 5/2006 | Djupesland |
| 2006/0219813 A1 | 10/2006 | Morrison |
| 2006/0240092 A1 | 10/2006 | Breitenkamp et al. |
| 2007/0056585 A1 | 3/2007 | Davies et al. |
| 2007/0068514 A1 | 3/2007 | Giroux |
| 2007/0074722 A1 | 4/2007 | Giroux et al. |
| 2007/0119451 A1 | 5/2007 | Wang et al. |

(56) References Cited

U.S. PATENT DOCUMENTS

| | | | |
|---|---|---|---|
| 2007/0131224 | A1 | 6/2007 | Giroux |
| 2007/0172517 | A1 | 7/2007 | Ben Sasson et al. |
| 2007/0202051 | A1 | 8/2007 | Schuschnig |
| 2008/0054099 | A1 | 3/2008 | Giroux et al. |
| 2008/0163874 | A1 | 7/2008 | Djupesland |
| 2008/0177246 | A1* | 7/2008 | Sullivan .................. A61M 5/30 604/116 |
| 2008/0178871 | A1 | 7/2008 | Genova et al. |
| 2008/0305077 | A1 | 12/2008 | Frey et al. |
| 2009/0229604 | A1* | 9/2009 | Pearson ............ A61M 15/0081 128/202.22 |
| 2009/0320832 | A1 | 12/2009 | Djupestand |
| 2011/0053859 | A1 | 3/2011 | Deadwyler et al. |
| 2012/0195959 | A1 | 8/2012 | Ishii |
| 2014/0083424 | A1 | 3/2014 | Haekman et al. |
| 2014/0170220 | A1 | 6/2014 | Cartt et al. |
| 2014/0343494 | A1 | 11/2014 | Hoekman et al. |
| 2015/0057287 | A1 | 2/2015 | Cook et al. |
| 2015/0216823 | A1 | 8/2015 | Chatterjee |
| 2015/0258178 | A1 | 9/2015 | Gong |
| 2016/0101245 | A1 | 4/2016 | Hoekman et al. |
| 2016/0228433 | A1 | 8/2016 | Haruta et al. |

FOREIGN PATENT DOCUMENTS

| | | | | |
|---|---|---|---|---|
| DE | | 19518580 | A1 | 11/1996 |
| DE | | 102013100473 | A1 | 7/2014 |
| EP | | 1165044 | A2 | 1/2002 |
| GB | | 806284 | A | 12/1958 |
| GB | | 1517642 | A | 7/1978 |
| JP | | H 08322934 | A | 12/1996 |
| WO | WO | 1986001731 | A1 | 3/1986 |
| WO | WO | 1999013930 | A1 | 3/1999 |
| WO | WO | 2000054887 | A1 | 9/2000 |
| WO | WO | 2001036033 | A2 | 5/2001 |
| WO | WO | 2002009707 | A1 | 2/2002 |
| WO | WO | 2007012853 | A1 | 2/2007 |
| WO | WO | 2008059385 | A2 | 5/2008 |
| WO | WO | 2014/179228 | A1 | 11/2014 |
| WO | WO-2014179228 | A1 * | 11/2014 | .......... A61M 11/006 |
| WO | WO | 2018/204217 | A1 | 11/2018 |

OTHER PUBLICATIONS

Baron, "Orally Inhaled Dihydroergotamine; Reviving and Improving a Classic", Future Neurology, May 2011, 11 pages.
Constantino, et al., "Intranasal administration of acetylcholinesterase inhibitors", BMC Neuroscience, Dec. 10, 2008, 3 pages.
European Patent Office, EP Office Action for 14727320.5, dated Nov. 9, 2016, 6 pages.
European Patent Office, EP Search Report for 09707800.0 dated Jul. 1, 2015, 12 pages.
European Patent Office, EP Search Report for 11818832.5 dated Sep. 24, 2014, 6 pages.
Hanson, et al., "Intranasal delivery of growth differentiation factor 5 to the central nervous system", Drug Delivery, 19(3):149-54, Feb. 2012, 7 pages.
Hoekman, J.D., "The Impact of Enhanced Olfactory Deposition and Retention on Direct Nose-to-Brain Drug Delivery", UMI Dissertation Publishing, Apr. 11, 2011, 181 pages.
Kumar, et al., "Nasal Drug Delivery: A Potential Route for Brain Targeting" The Pharma Innovation Journal, vol. 2, No. 1, Mar. 2013. 9 pages.
Ozsoy, et al., "Nasal Delivery of High Molecular Weight Drugs", Molecules Journal, Sep. 23, 2009, 26 pages.
Parvathi, "Intranasal Drug Delivery to Brain: An Overview," published in the International Journal of Research in Pharmacy and Chemistry 2012, 2(3), 7 pages.
PCT International Search Report and Written Opinion, PCT Application No. PCT/US2020/033282, dated Aug. 10, 2020, 16 pages.
PCT Search Report and Written Opinion, PCT Application No. PCT/US2011/048435, dated Mar. 27, 2012, 14 pages.
PCT International Search Report, PCT Application No. PCT/US/2009/033468, dated Dec. 2, 2009, 5 pages.
Renner, et al., "Intranasal delivery of growth differentiation factor 5 to the central nervous system," Drug Delivery, Feb. 2012, 7 pages.
Stevens, et al., "Systemic and Direct Nose-to-Brain Transport Pharmacokinetic Model for Remoxipride after Intravenous and Intranasal Administration", in "Drug Metabolism and Disposition", The American Society for Pharmacology and Experimental Therapeutics, 2011, vol. 39, No. 12, 8 pages.
Talegaonkar, et al., "Intranasal delivery: an approach to bypass the blook brain barrier", Indian J Pharmacol, Jun. 2004, vol. 36, Issue 3, 8 pages.
Westin et al., "Direct Nose to Brain Transfer of Morphine After Nasal Administration to Rats", Pharmaceutical Research, vol. 23, No. 3, Mar. 2006, 8 pgs.
Westin, "Olfactory Tranfser of Analgesic Drugs After Nasal Administration", Digital Comprehensive Summaries of Uppsala Dissertations from the Faculty of Pharmacy 55, May 11, 2007, 66 pages.
Yamada, et al., "Nose-to-brain delivery of TS-002, prostaglandin D2 analogue", Journal of Drug Targeting, Jan. 2007, 9 pages.
Yimam, et al., "Effects of lipid association on lomustine (CCNU) administered intracerebrally to syngeneic 36B-10 rat brain tumors", Cancer Letters 244(2), Dec. 2006, 9 pages.
Ying, "The nose may help the brain: intranasal drug delivery for treating neurological diseases" Future Medecine, 3(1), Jan. 2008, 4 pages.
Zhang, et al., "The brain targeting efficiency following nasally applied MPEG-PLA nanoparticles in rats", Journal of Drug Targeting, Jun. 2006, 11 pages.
European Patent Office, Extended European Search Report, European Patent Application No. 20808724.7, dated May 23, 2023, nine pages.

* cited by examiner

SINGLE-USE NASAL DELIVERY DEVICE

CROSS-REFERENCE TO RELATED APPLICATION

This application claims the benefit of provisional U.S. Patent Application No. 62/849,735, filed on May 17, 2019, which is incorporated by reference herein in its entirety for all purposes.

BACKGROUND

This disclosure relates generally to a drug delivery device, and specifically to a nasal drug delivery device for delivering drugs to the nasal cavity of a user.

Current devices often rely on the patient to coordinate their breath with actuation of the device for proper use. This can be an ineffective means of drug delivery when the patient is inexperienced with the device, or when a caregiver is administering the device to the patient. Further, current devices often require a priming step before use, which can negatively affect device efficacy and proper dosing.

SUMMARY

Embodiments relate to a single-use device for delivery of medication into the nasal cavity of a human or other mammal. The nasal cavity is regarded as a useful cavity for absorption of medication. The single-use device enables a single dose of medication to be delivered to a nasal cavity before being disposed of. Further, the device enables medication to be delivered in a reproducible manner while being simple and intuitive for a patient or caregiver to use. For example, using the single-use delivery device, medication is provided to patients using a single actuation step. In addition, the single-use delivery device reduces the chances of inadvertent overdosing or misuse relative to multi-use devices because second dosing is improbable.

In some embodiments, the single-use device utilizes a unit dose container of propellant to push medication into the nasal cavity. Use of a propellant in the device ensures that medication may be administered by a patient and/or caregiver without the need for the patient to coordinate their breath with the actuation of the device. In addition, by using a unit dose container of propellant, the device does not need to be primed, and the amount of propellant used is controlled and consistent on a dose-to-dose basis.

In an embodiment, a nasal delivery device for delivery of a compound includes a propellant canister containing a propellant capable of propelling the compound to a nasal cavity of a user. The propellant canister is displaceable between an unactuated position and an actuated position within a housing body of the device. The device further includes an actuation element. The actuation element includes an actuation lever that is configured to displace the propellant canister from the unactuated position to the actuated position. In the embodiment, the nasal delivery device also includes a puncture element. The puncture element may be positioned to puncture the propellant canister, which causes the release of the propellant from the propellant canister when the propellant canister is driven from the unactuated position to the actuated position by the actuation element. In the embodiment, the device further includes a dose holding chamber containing a unit dose of the compound. The dose holding chamber is positioned such that propellant flows into the dose holding chamber and causes the compound to be propelled from the dose holding chamber to the nasal cavity of the user.

The nasal delivery device may also include a diffuser positioned between the propellant canister and the dose holding chamber such that the diffuser diffuses the propellant upon its release from the propellant canister. The device may also include a nozzle positioned such that the compound flows through the nozzle and out one or more outlet orifices of the nozzle upon being propelled from the dose holding chamber for delivery of the compound to the nasal cavity.

In some embodiments, the actuation lever may be an L-shaped lever. A first member of the L-shaped lever may be positioned to receive a contact force from an actuation button of the actuation element. A second member of the L-shaped lever may be perpendicular to the first member, and may apply a contact force to the propellant canister upon actuation of the actuation button. Further, the actuation element may include a securing latch that is configured to release the actuation lever upon actuation of the actuation element from a mating interface of the securing latch and the actuation lever.

In some embodiments, the actuation element includes an actuation button that, when depressed, drives the propellant canister into the puncture element, thereby puncturing the propellant canister. Further, the actuation element may include a sliding element exposed from the housing body that is slideable between an unactuated position that enables positioning of the propellant canister in the unactuated position and an actuated position that forces the propellant canister to the actuated position. In addition, the device may include a removeable cap that maintains the actuation element in an unactuated position, a lock to maintain the actuation element in an actuated position, and/or a use indicator that provides an indication that the actuation element is in the actuated position.

DETAILED DESCRIPTION

The figures depict embodiments of the present disclosure for purposes of illustration only. One skilled in the art will readily recognize from the following description that alternative embodiments of the structures and methods illustrated herein may be employed without departing from the principles, or benefits touted, of the disclosure described herein.

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise:

As used herein the specification, "a" or "an" may mean one or more.

A "diffuser" refers to and encompasses a component for dispersing or deflecting a compound in various directions.

A "propellant" shall refer to and encompass a compound that acts as a vehicle for creating propulsion or thrust.

A "user" or "subject" shall refer to and encompass a human or other animal. For example, the animal may be a primate or a non-primate and may include a rabbit, bovine, equine, pig, rat, mouse, dog or cat.

The device may be used in treatment, prevention, palliative care for humans and veterinary purposes. The device may be used in research and industrial uses. For example, the device may be used to deposit compound in agricultural settings.

FIGS. 1A-1D illustrate various views of a single-use nasal drug delivery device 100. The device 100 is designed to deliver a consistent mass of compound into the nasal cavity. For example, but not limited to, the compound may be an intranasal formulation in a liquid or suspension form. In some embodiments, the device 100 targets a specific region of the nasal cavity, such as the upper regions of the nasal cavity (e.g., the middle and superior turbinate regions and/or the olfactory region).

Figure 1A:
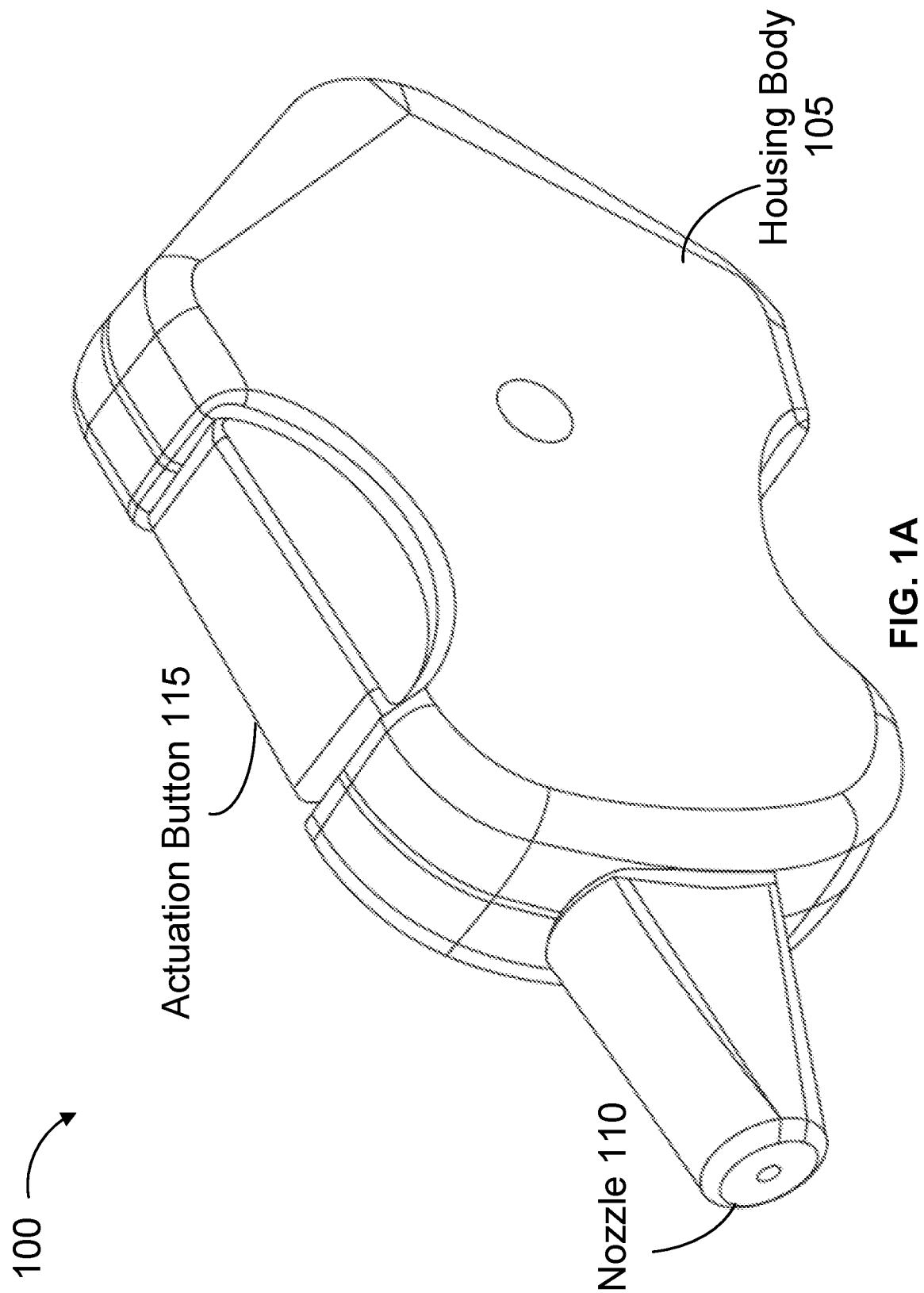
FIG. 1A illustrates an isometric view of a single-use nasal drug delivery device, according to one embodiment.
Figure 1B:
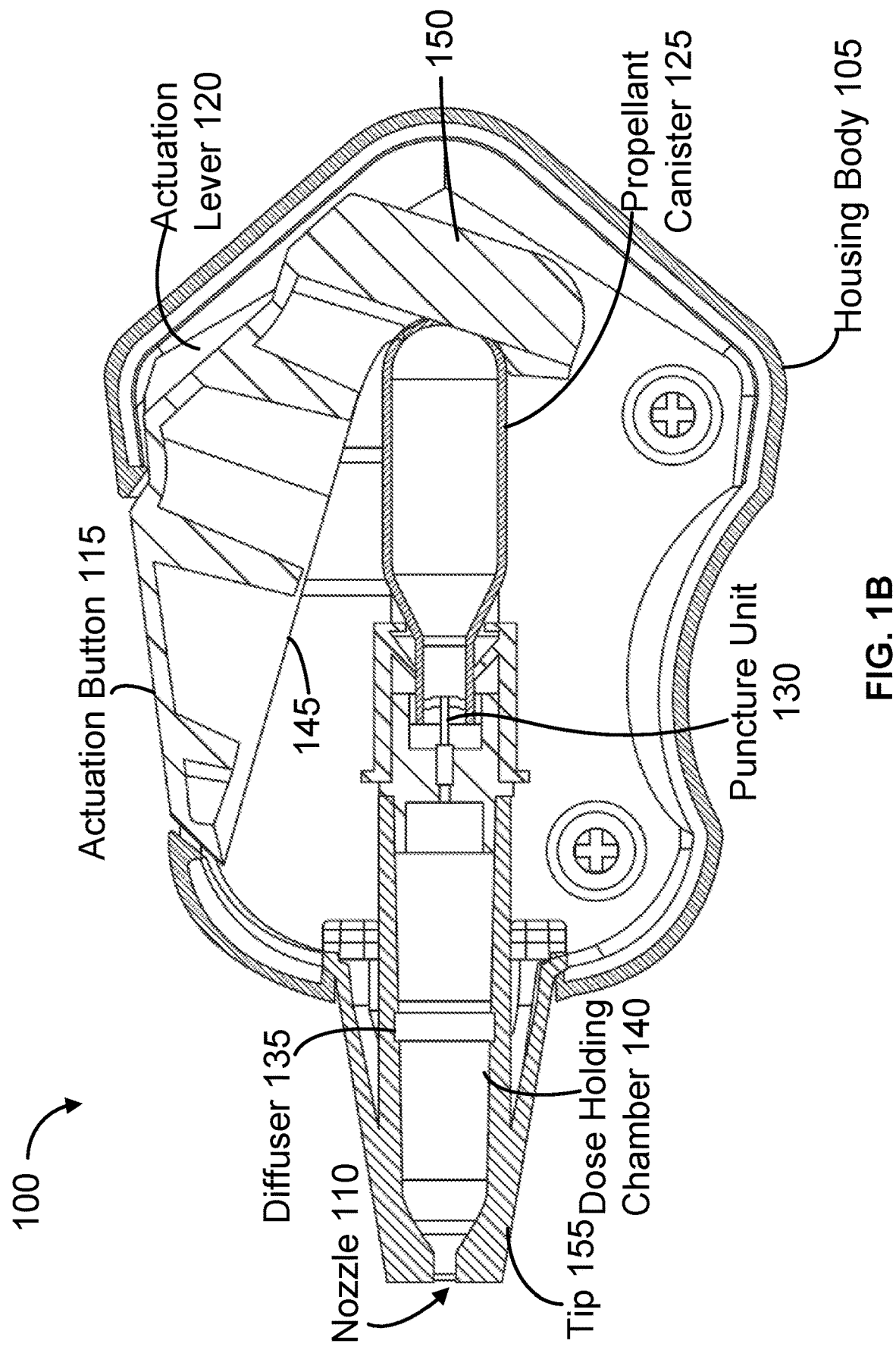
FIG. 1B illustrates a cross-sectional views of the single-use nasal drug delivery device, according to one embodiment.

FIG. 1A illustrates a perspective view of the single-use nasal drug delivery device 100 and FIG. 1B illustrates a cross-sectional view. The device 100 includes a housing body 105, a nozzle 110, and an actuation element with an actuation lever. In the embodiment shown, the actuation element also includes an actuation button 115, disclosed in detail below. In other embodiments, the actuation element may include a sliding element, disclosed in detail with reference to FIG. 4. The housing body 105 is designed to be held in a hand administering the compound to the nasal cavity of the user. The user actuates the device 100 in a single actuation step by depressing the actuation button 115. Upon actuation, the compound contained within the device 100 propels out of the nozzle 110 and into the nasal cavity of the user. For example, the user may place the nozzle 110 into their naris and actuate the actuation button 115 to release the propellant driven compound into the nasal cavity. Once the compound is administered, the device may be disposed of.

In some embodiments, a diameter of the nozzle 110 tapers toward the outlet orifice of the nozzle 110. This configuration may beneficially increase the velocity of the drug compound before it exits the outlet orifice. In addition, this configuration may beneficially decrease the plume width. Decreased plume widths may enable the compound to be propelled further into the nasal cavity and into the upper regions of the nasal cavity (e.g., the middle and superior turbinate regions and/or the olfactory region). In alternative embodiments, the nozzle 110 may be cylindrical or conical in shape.

Further, the design of the nozzle 110 may be optimized for various compounds having different characteristics. For example, the diameter of the nozzle 110, the angle and/or shape of the taper, and/or the diameter of the outlet orifice may be modified (e.g., increased or decreased) to suitably deliver a compound to the upper nasal cavity. As an example, larger nozzles and/or outlet orifices of the nozzles may be used for some drug compounds in powder form to prevent clogging within the nozzle 110. In addition, the number and configuration of outlet orifices in the nozzle 110 may vary to suitably deliver the compound to the upper nasal cavity. For example, the nozzle 110 may include one or more outlet orifices (e.g., one or more outlet orifices, two or more outlet orifices, three or more outlet orifices, four or more outlet orifices, five or more outlet orifices, six or more outlet orifices, seven or more outlet orifices, etc.). In some embodiments, the nozzle 110 is manufactured with a removable seal, such as a metal or plastic seal, to keep the compound in the device 100 until actuation. The removable seal may be in the shape of a pull tab, or may have other suitable geometries for sealing the outlet orifice of the nozzle 110 and providing a portion that a user may grab to remove the removable seal from the nozzle 110.

While the actuation button 115 shown is on the top of the device 100, the actuation button 115 may be placed on the bottom, side, front, and/or back of the device 100. Further, the actuation element may include an electrical motor (e.g., a battery-operated motor), a spring mechanism, and the like. In some embodiments, the device 100 is actuated in a single actuation step. In other embodiments, the device 100 is actuated in one or more actuation steps. For example, the device 100 may require a priming step to load a spring-loaded actuation lever.

As shown in FIG. 1B, the housing body 105 contains an actuation lever 120, a propellant canister 125, puncture unit 130, a diffuser 135, and a dose holding chamber 140. In the illustration shown, the actuation button 115 is connected to the actuation lever 120 and exposed from the housing body 105. When the actuation button 115 is depressed, the actuation lever 120 pushes the propellant canister 125 towards the nozzle 110 end of the device 100 causing the propellant canister 125 to encounter the puncture unit 130. When a threshold force is achieved (actuation of the device), the puncture unit 130 punctures the propellant canister 125, which allows the propellant contained in the propellant canister 125 to be released. The propellant flows towards and through the diffuser 135, into the dose holding chamber 140. As the propellant flows into the dose holding chamber 140, it pushes the compound in the dose holding chamber 140 out of the nozzle 110 such that the compound exits the nozzle 110 (e.g., through one or more outlet orifices of the nozzle 110). The propellant may follow the compound out of the nozzle 110 or may at least partially mix with the compound as it exists the nozzle 110.

In some embodiments, the propellant canister 125 is welded together to ensure that the propellant stays within the propellant canister 125 until time of use. A welded seal can require significant force to puncture or break. The actuation lever 120 reduces the amount of force applied by the user on the actuation button 115 to puncture the propellant canister 125 and actuate the device 100 relative to the direct force sufficient to puncture the propellant canister 125. The length of the actuation lever 120 may be designed differently in different embodiments dependent on the desired amount of force from the user intended to be sufficient to actuate the device 100, discussed in detail below with reference to FIGS. 5-6. Alternatively, or additionally, other suitable mechanisms may be used to reduce the force required by the user to actuate the device, such as spring mechanisms, motors, etc.

The actuation lever 120 is a substantially L-shaped lever arm. A first member 145 of the actuation lever 120 is positioned to receive a contact force from the actuation button 115. A second member 150 of the actuation lever 120 is perpendicular to the first member. The second member 150 of the actuation lever 120 applies a contact force to the propellant canister 125 upon actuation of the actuation button 115. The contact force causes the propellant canister 125 to move from an unactuated position to an actuated position, which causes the propellant canister to come into contact with the puncture unit 130. In some embodiments, the first member 145 of the actuation lever 120 and the second member 150 of the actuation lever are of unibody construction together with the actuation button 115. In other embodiments, the first member 145 of the actuation lever 120, the second member 150 of the actuation lever, the actuation button 115, or a combination thereof, may be distinct and separate components. Alternative embodiments of actuations levers are discussed in detail below, with reference to FIG. 4.

Figure 1C:
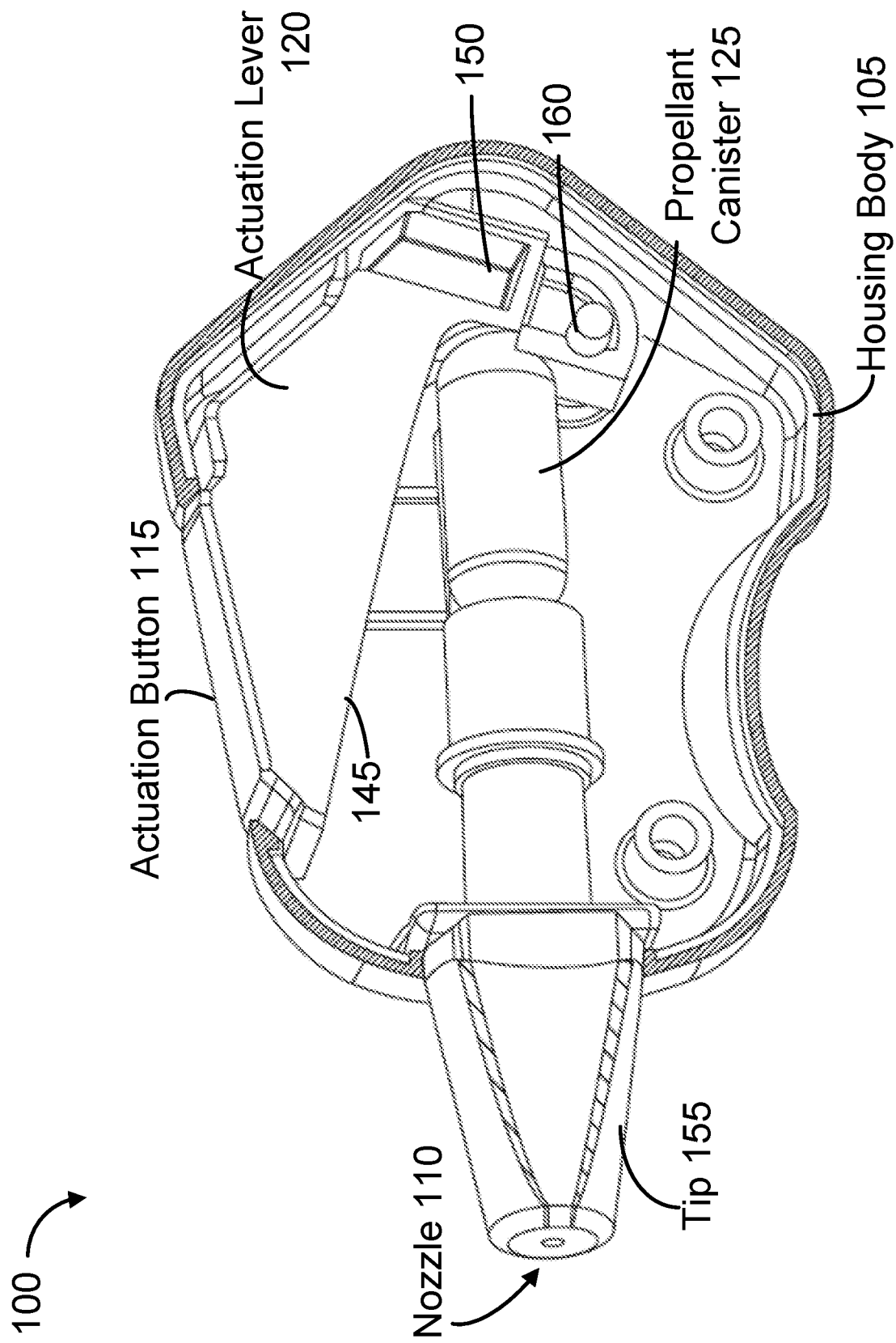
FIG. 1C illustrates a first partial view of a single use nasal drug delivery device, according to one embodiment.
Figure 1D:
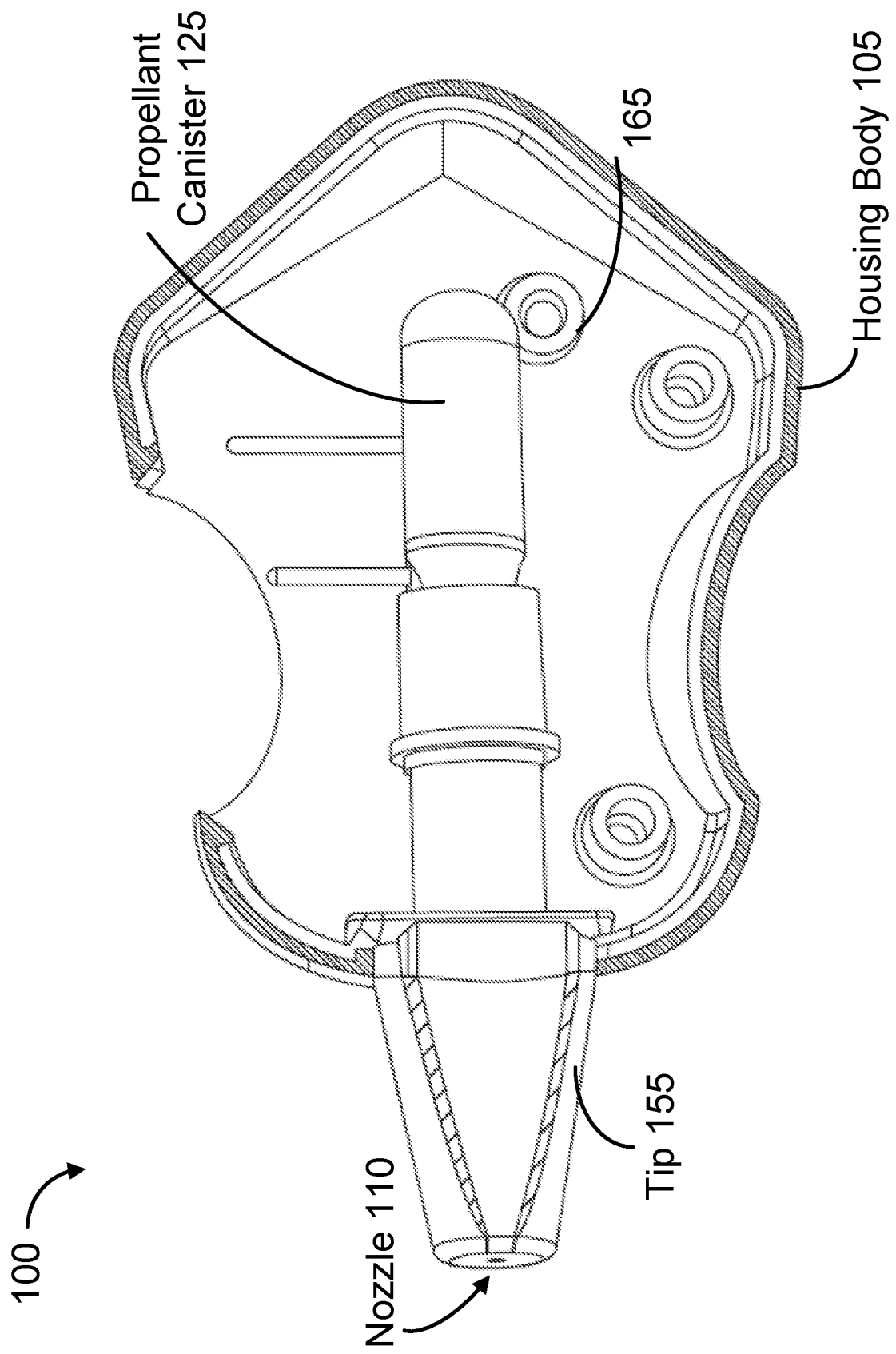
FIG. 1D illustrates a second partial view of a single use nasal drug delivery device, according to one embodiment.

FIG. 1C illustrates a first partial view with the front cover of the housing body 105 removed, and FIG. 1D illustrates a second partial view with the front cover of the housing body 105 and the actuation lever 115 removed to further illustrate the actuation mechanism. The actuation lever 120 includes or is attached to one or more pegs 160 that guide the movement of the actuation lever 120 within the device 100. The pegs 160 fit into the raised holes 165, shown in FIG. 1D, of the housing body 105 such that the one or more pegs 160 may freely rotate within the hole 165, but cannot move laterally. As a result, the one or more pegs 160 act as pivots points along which the actuation lever 120 may rotate. Upon actuation of the device 100, the actuation lever 120 rotates about the one or more pegs 160.

The propellant contained in the propellant canister 125 is a fluid propellant, such as a liquid propellant or a gaseous propellant. Propellants include pharmaceutically suitable propellants such as hydrofluoroalkane (HFA) including but not limited to HFA, HFA 227, HFA 134a, HFA-FP, HFA-BP and the like HFA's. Additional examples of suitable propellants include nitrogen or choloroflourocarbons (CFC). Additionally, the propellant may be pressurized. For example, propellants may be pressurized air (e.g. ambient air), pressurized nitrogen, pressurized carbon dioxide, or pressurized argon.

The propellant canister 125 may have a capacity for distributing propellant for a certain number of doses. In some embodiments, the propellant canister 125 is a unit dose propellant canister 125 such that the device 100 may be a single-use device. In these embodiments, the device 100 may be disposed of after a single dosing, and/or the propellant canister 125 may be replaced with a new canister. In some embodiments, the propellant canister 125 may include propellant for multiple actuations of the device. The amount of propellant released upon actuation may be between about 5 µl and 250 µl, inclusive of endpoints, of propellant.

The puncture unit 130 is designed to puncture the propellant canister 125 to create an opening in the propellant canister 125. The puncture unit 130 may comprise a sharp point, a sharp angle, a blade-like edge, or other suitable geometries for puncturing the propellant canister 125. The puncture unit 130 may be configured to puncture a puncture area of the propellant canister 125, such as a dimple of the propellant canister 125. In some embodiments, the device 100 includes multiple puncture units that are each suitable for puncturing the propellant canister 125 upon actuation. Alternatively, or additionally, the device may include one or more additional puncture units designed to puncture the dose holding chamber 140. For example, an additional puncture unit may puncture a distal end of the dose holding chamber 140 upon actuation. As another example, an additional puncture unit may puncture a proximal end of the dose holding chamber 140 upon actuation.

The diffuser 135 diffuses propellant released from the propellant canister 125. In one aspect, a majority of the propellant is diffused via the diffuser 135. In another aspect, a minority of the propellant is diffused via the diffuser 135. In some embodiments, the diffuser 135 is a porous member. An example of a diffuser 135 includes a frit, a plurality of frits, or a diffuser member or combinations thereof.

The diffuser 135 may act as a one-way check-valve to keep a liquid or dry compound in the dose holding chamber 140 from coming into contact with the propellant canister 125. For example, the diffuser 135 may prevent the compound from travelling into the propellant canister 125, while allowing the propellant to travel through the diffuser and push the compound in the opposite direction towards the nozzle. The diffuser 135 may also serve to reduce the velocity and/or pressure of the propellant exiting the propellant canister 125. The diffuser 135 may also serve to increase the temperature of the propellant exiting the propellant canister 125. Additionally, or alternatively, the diffuser 135 may convert propellant from a liquid to a gas. For example, the diffuser 135 may expand the propellant from a liquid state to a gaseous state. The gaseous propellant may aerosolize the compound and propel the aerosolized compound through the dose holding chamber 140 and out of the nozzle 110. In some embodiments, the device 100 does not include a diffuser. In these embodiments, the propellant flows from the propellant canister 125, through the dose holding chamber 140, and out of the nozzle 110, propelling the compound out of the nozzle 110 in the process.

The dose holding chamber 140 contains one or more unit doses of a compound. The compound may treat a variety of conditions, including but not limited to migraines, epilepsy, pain, agitation, Parkinson's disease, opioid overdose, addiction, narcolepsy, and/or sleeping disorders. Examples of the compound may include, but are not limited to olanzapine, levodopa, dihydroergotamine, sumatriptan, zolmitriptan, diazepam, midazolam, naloxone, dexameditimodine, morphine, and/or fentanyl. Alternative or additional compounds may be used in alternative embodiments.

In some embodiments, the device 100 may include a tip 155 that houses the nozzle 110, diffuser 135, and dose holding chamber 140.

Figure 2A:
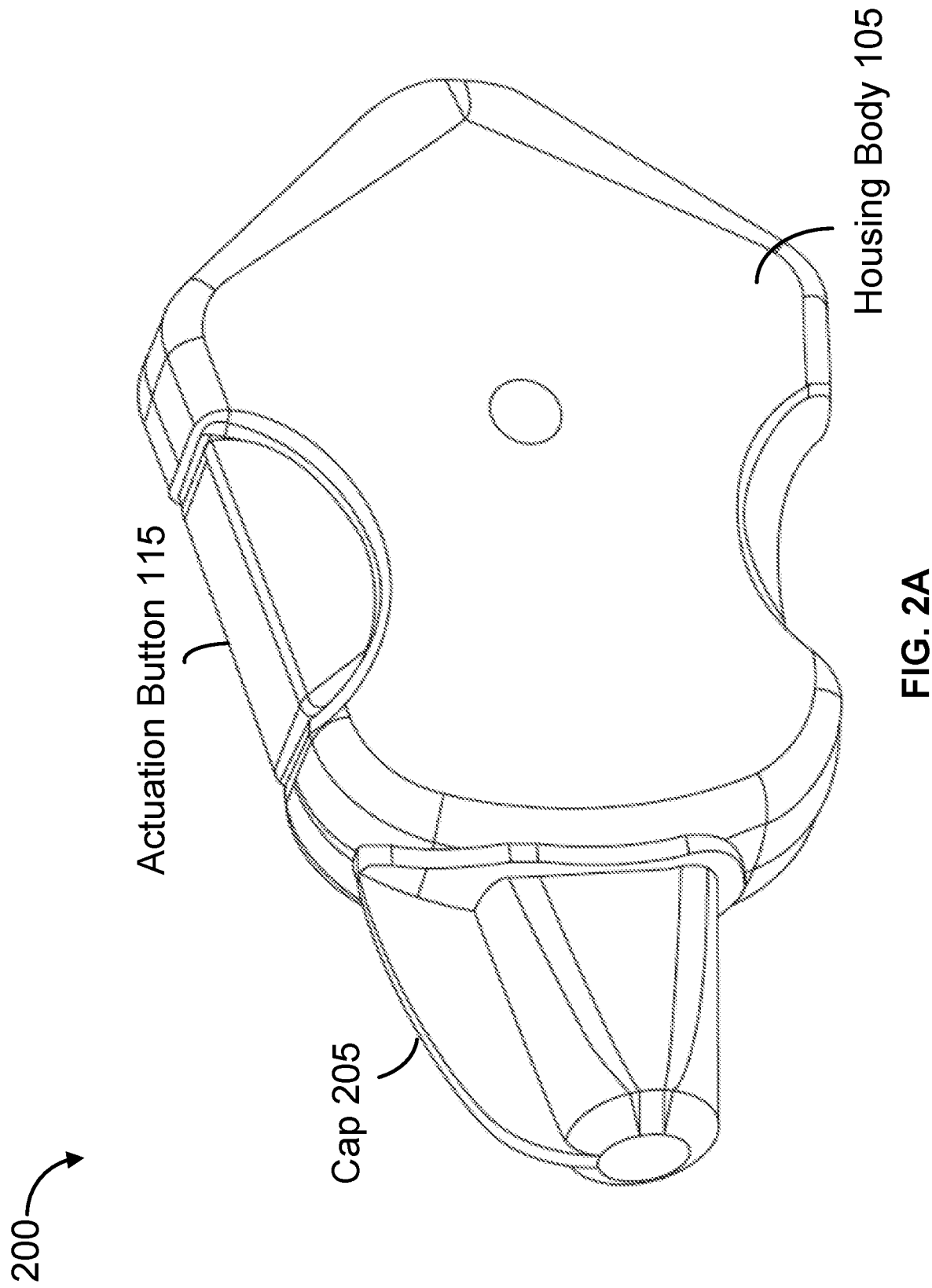
FIG. 2A illustrates an isometric view of a single-use nasal drug delivery device with a cap, according to one embodiment.
Figure 2B:
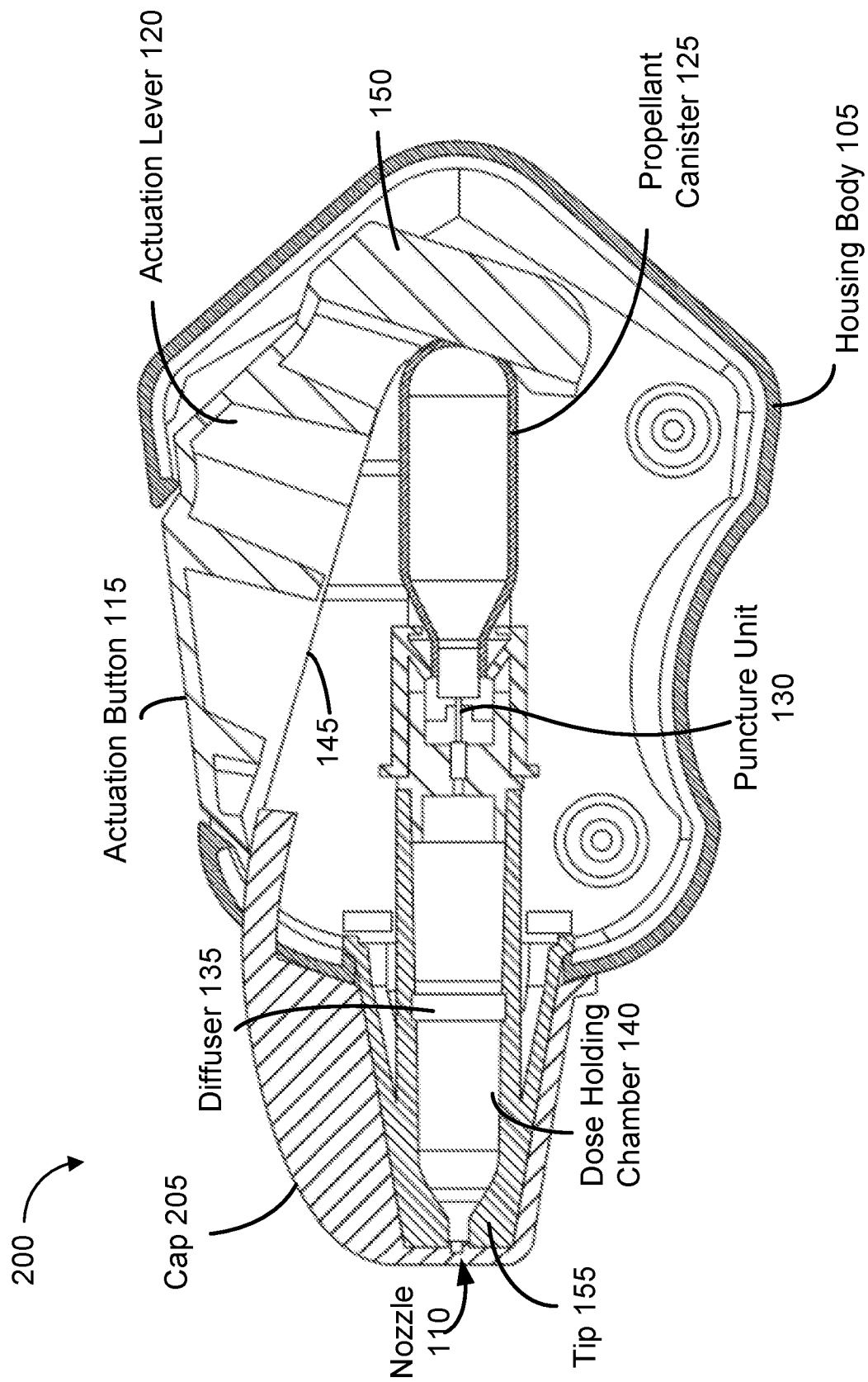
FIG. 2B illustrates a cross sectional view of the single-use nasal drug delivery device shown in FIG. 2A, according to one embodiment.

FIGS. 2A and 2B illustrate a perspective view and a cross-sectional view, respectively, of a single-use nasal drug delivery device 200 with a cap 205. The cap covers the tip 155 and nozzle 110 of the device 200. The cap 205 blocks the nozzle 110 to prevent anything from getting into or out of the device 200. The cap 205 includes an extending member that extends through a slit in the housing body 105 to prevent the actuation button 115 from being depressed. In this way, the cap 205 prevents the actuation lever 120 from being actuated prematurely (e.g., during manufacturing, shipping, handling, etc.). In addition, the cap 205 may provide an indication to the user that the device 100 has not been actuated. To actuate the device 100, the user removes the cap by pulling the cap 205 away from the device 100 and/or rotating the cap 205 along one or more threads to remove the cap 205 and unlock the actuation lever 120. Further, a pull tab may be implemented to provide similar functionality to the cap 205. In embodiments that include a pull tab, the user removes the pull tab to unlock the actuation lever 120 from an unactuated position.

The device 200 may further include a lock (not shown), such as a ratcheting lever lock, to lock the actuation lever 120 in an actuated (or partially actuated) position after the actuation lever 120 has rotated by a predetermined distance in an inward direction during actuation. The lock locks the actuation lever 120 in place after the device 200 has been actuated, preventing further actuation of the device 200. The lock may be placed along various locations of actuation lever 120. For example, the lock may comprise a ratcheting mechanism placed on the pivot point of the actuator lever 120 to enable rotation from an unactuated to an actuated position but to prevent rotation of the actuation lever 120 in a reverse direction. Thus, following actuation, the lock maintains the actuation lever 120 in the actuated position. Alternatively, or additionally, a lever lock may be placed near the actuation button 115 end of the actuation lever 120. In these embodiments, once the actuation button 115 is depressed, the lock latches over the depressed actuation button 115 to prevent the actuation lever 120 from lifting back up and therefore locks the actuation lever in the actuated position. Further, the device 200 may include a use indicator (not shown). The use indicator provides a visual indication that the device 200 has been actuated. Examples of use indicators include a cutout in the housing body 105 and/or a physical feature that protrudes from the housing body 105, each of which may display one color before the device has been actuated and a different color after the device has been actuated. The use indicator may be colored metal, colored plastic, an LED, and the like. Alternatively, the use indicator may be any suitable visual indicator that provides an indication the device 200 has been actuated.

Figure 3A:
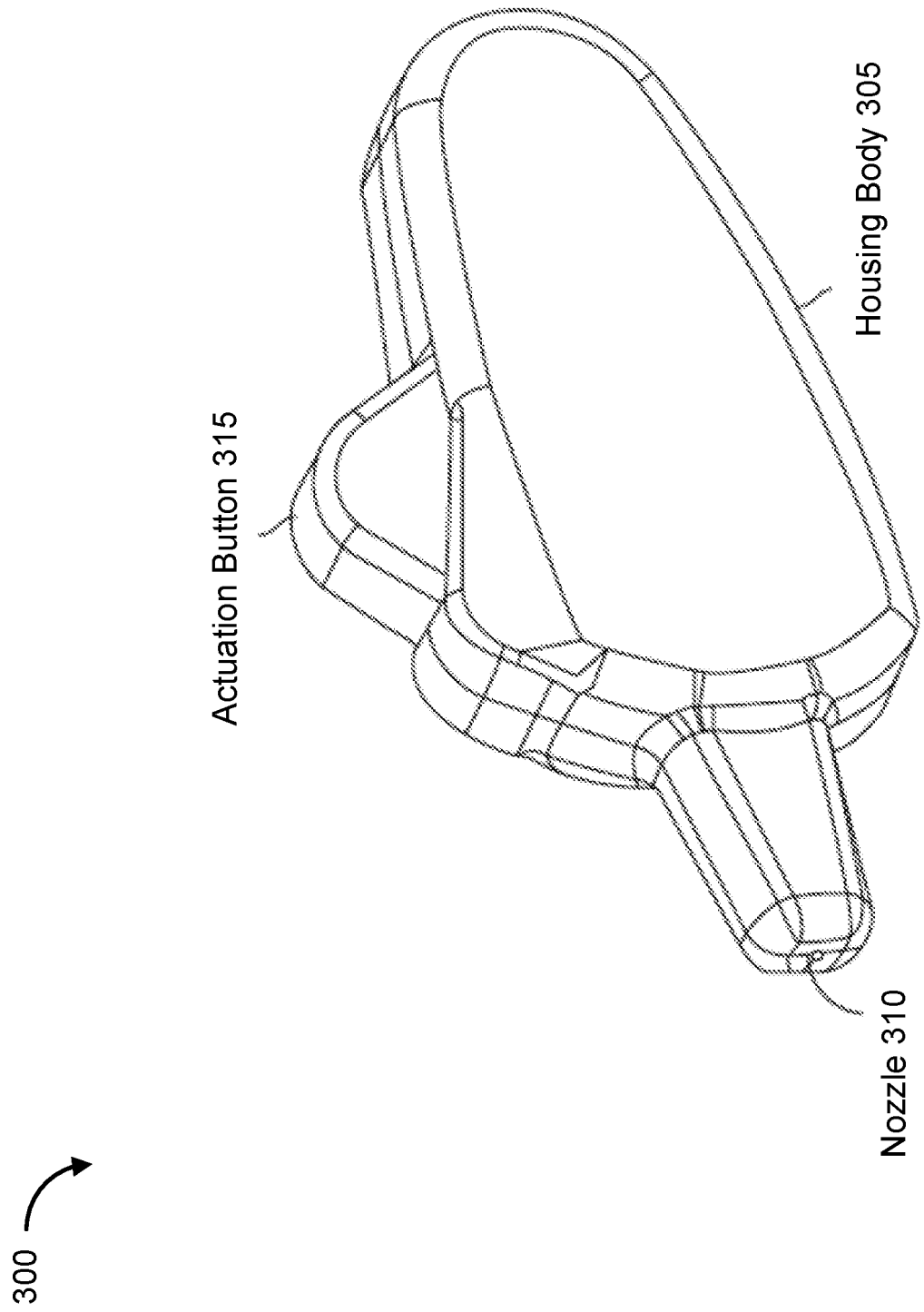
FIG. 3A illustrates an isometric view of a variation of a single-use nasal drug delivery device, according to one embodiment.
Figure 3B:
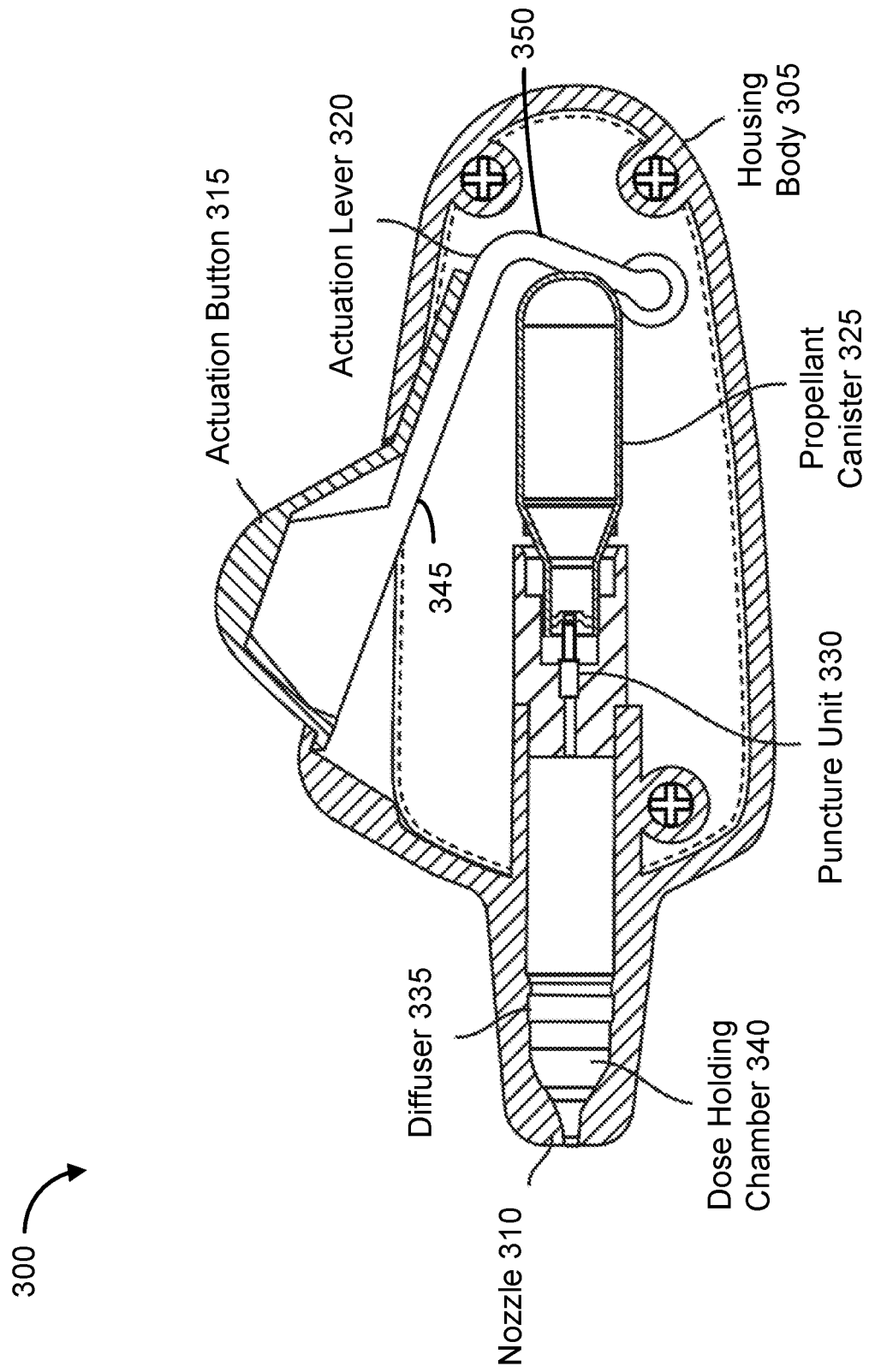
FIG. 3B illustrates a cross sectional view of the single-use nasal drug delivery device shown in FIG. 3A, according to one embodiment.

FIGS. 3A-3B illustrate a perspective view and a cross-sectional view, respectively, of a variation of a single-use nasal drug delivery device 300. In the embodiment shown, the device 300 includes a housing body 305, a nozzle 310, and an actuation element with an actuation lever. In the embodiment shown, the actuation element includes an actuation button 315. The housing body 305 contains an actuation lever 320, a propellant canister 325, a puncture unit 330, a diffuser 335, and a dose holding chamber 340.

Some of the components in the device 300 shown have a different form factor than the devices shown in FIGS. 1A-2B. For example, in the device 300, the actuation button 315 protrudes from the actuation lever 320 so that it extends outside the hosing body 305, while in the device 100, the surface of the actuation button 115 is approximately planar with the surface of the housing body 105. Furthermore, the dose holding chamber 340 in the device 300 may be a different size and/or shape than the dose holding chamber 140 of the device 100. The device 300 may furthermore have a housing body 305 with a different general form factor than the device 100. However, apart from these cosmetic differences, the devices 100, 300 are structured and operate substantially equivalently, and the components of the devices 100, 300 unless otherwise indicated may be functionally the same or similar.

Figure 4:
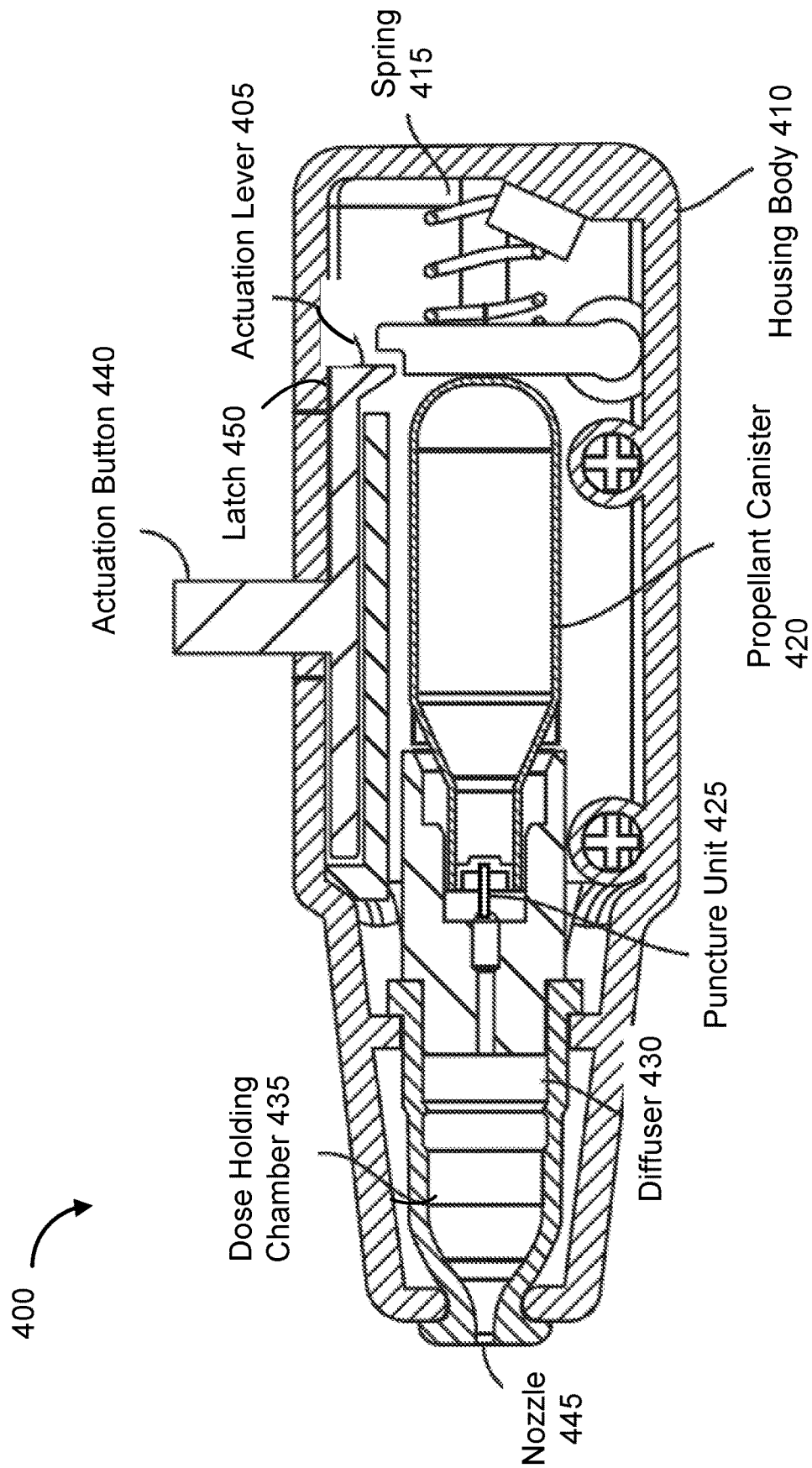
FIG. 4 illustrates a cross sectional view of a single-use nasal drug delivery device with a spring forced actuation lever, according to one embodiment.

FIG. 4 illustrates a cross sectional view of a single-use nasal drug delivery device 400 with a spring forced actuation lever 405. In the device 400 shown, the housing body 410 contains an actuation lever 405, a spring 415, a propellant canister 420, a puncture unit 425, a diffuser 430, and a dose holding chamber 435. The device 400 further includes an actuation button 440 configured to actuate the device 400 and a nozzle 445 through which a compound contained in the dose holding chamber 435 is expelled. The device 400 may further include a cap, a lock, and/or a use indicator.

In the device 400 shown, the actuation button 440 is a slideable element that includes a securing latch 450, and the actuation lever 405 is spring 415 loaded. The actuation button 440 is connected to the actuation lever 405, which is contained within the housing body 410. When the actuation lever 405 is pushed by the compressed spring 415, the actuation lever 405 is also being held in place by the actuation button 440 at the interface of the actuation lever 405 and the securing latch 450.

When a user slides the actuation button 440 in a direction away from the nozzle 445, the actuation button 440 physically releases the actuating lever 405 at the mating interface of the actuation lever 405 and the securing latch 450. The spring force then drives the actuator lever 405 against the propellant canister 420, which forces propellant canister against the puncture unit 425. The puncture unit 425 punctures the propellant canister 420, which releases the propellant contained in the propellant canister 420.

The released propellant flows towards and through a diffuser 430, into the dose holding chamber 435, and out of the nozzle 445 (e.g., through one or more outlet orifices of the nozzle 445). Once the propellant enters the dose holding chamber 435, the propellant pushes the compound contained in the dose holding chamber 435 out through the nozzle 445 itself.

Similar to the devices shown in FIGS. 1A-3B, the propellant contained in the propellant canister 420 is a fluid propellant, such as a liquid propellant or a gaseous propellant. Propellants include pharmaceutically suitable propellants. Some examples of pharmaceutically suitable propellants include hydrofluoroalkane (HFA) including but not limited to HFA, HFA 227, HFA 134a, HFA-FP, HFA-BP and the like HFA's. Additional examples of suitable propellants include nitrogen or choroflourocarbons (CFC). Additionally, the propellant may be pressurized. For example, propellants may be pressurized air (e.g. ambient air), pressurized nitrogen, pressurized carbon dioxide, or pressurized argon.

In addition, the diffuser 430 may act to keep a liquid or dry compound in the dose holding chamber 430, serve to reduce the velocity and/or pressure of the propellant exiting the propellant canister 420, serve to increase the temperate of the propellant exiting the propellant canister 420, and/or convert propellant from a liquid to a gas.

In some embodiments, the actuation button 440 is configured such that the device 400 is actuated by depressing the actuation button 440 in a direction towards the housing body. Upon depression of the actuation button 440, the actuation lever 405 is released from an unactuated position to an actuated position. This causes the propellant canister 420 to contact the puncture unit 425, which punctures the propellant canister 420. In these embodiments, the actuation lever 405 may be spring loaded. While the actuation button 440 shown is on the top of the device 400, the actuation button 440 may be placed on the bottom, side, front, and/or back of the device 400. Further, in some embodiments, the device 400 is actuated in a single actuation step. In other embodiments, the device 400 is actuated in one or more actuation steps. For example, the device 400 may require a priming step to load the spring 415.

Figure 5:
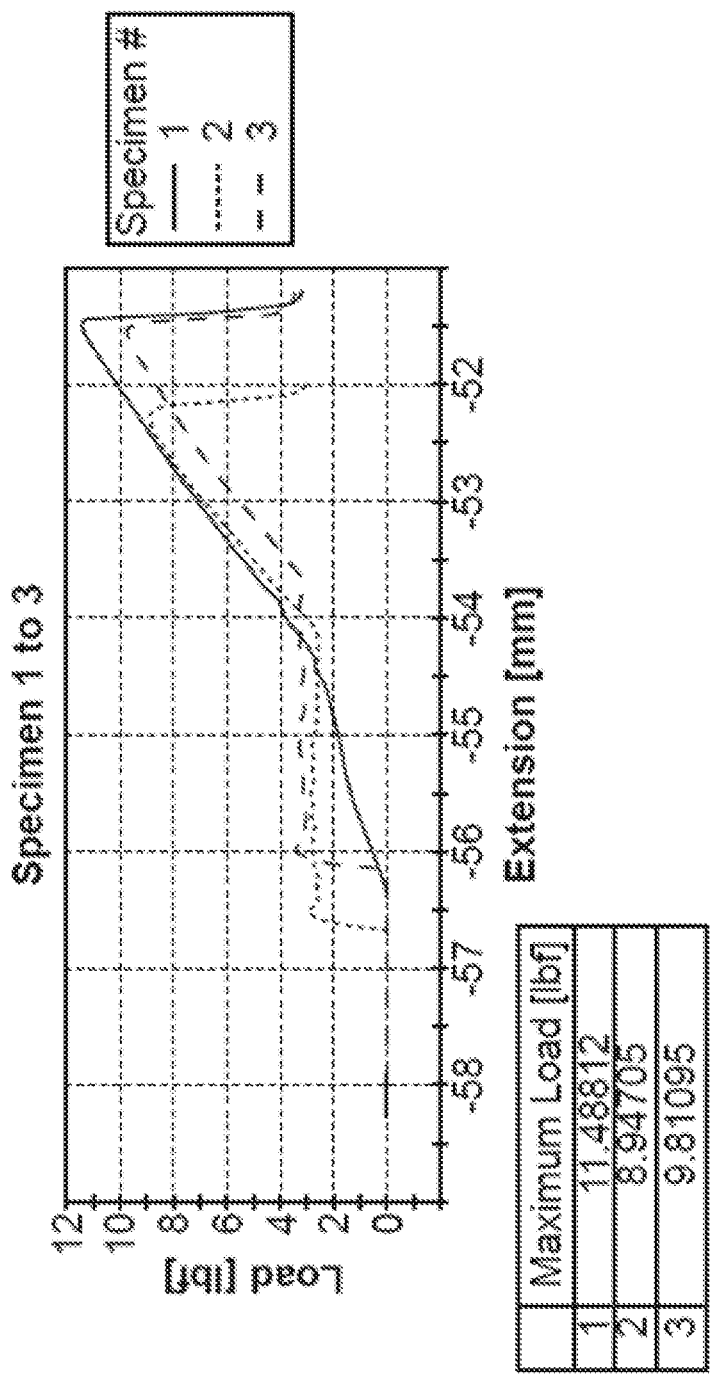
FIG. 5 illustrates actuation force data from a single-use nasal drug delivery device with a short actuation lever.

FIG. 5 illustrates actuation force data from a single use nasal drug delivery device with a short actuation lever similar to the devices shown in FIGS. 1A-D and 3A-B. As seen in FIG. 5, by using an actuation lever, the force required to actuate the device is between 8 and 10 lbs. of force.

Figure 6:
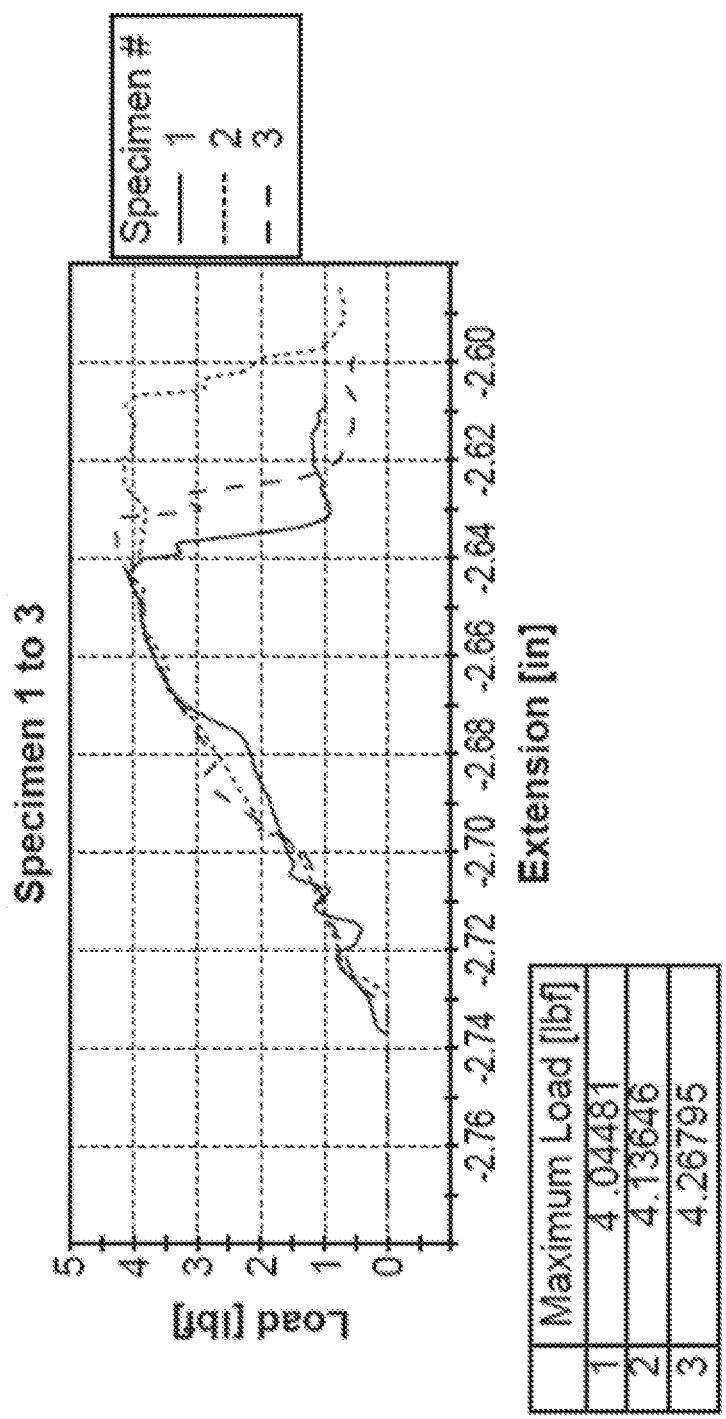
FIG. 6 illustrates force data from a single-use nasal drug delivery device using a long actuation lever.

FIG. 6 illustrates force data from a single-use nasal drug delivery device using a long actuation lever similar to the devices shown in FIGS. 1A-D and 3A-B. The devices used to generate the data in FIG. 6 are similar to those used to develop the data in FIG. 5 except that they have a longer actuation lever. With these devices, the amount of force required to actuate the devices is roughly 4 lbs. of force showing that the actuation lever can be designed to reduce the amount of force required to actuate the device.

Additional Configuration Information

The foregoing description of the embodiments of the disclosure has been presented for the purpose of illustration; it is not intended to be exhaustive or to limit the disclosure to the precise forms disclosed. Persons skilled in the relevant art can appreciate that many modifications and variations are possible in light of the above disclosure.

The language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based hereon. Accordingly, the disclosure of the embodiments is intended to be illustrative, but not limiting, of the scope of the disclosure, which is set forth in the following claims.

The invention claimed is:

1. A device for delivery of a compound to a nasal cavity, the device comprising:
   a housing body;
   a propellant canister in the housing body capable of containing a propellant which is different from the compound, the propellant canister displaceable between an unactuated position and an actuated position;
   a puncture element in the housing body positioned to puncture the propellant canister and cause release of the propellant from the propellant canister when the propellant canister is displaced to the actuated position;
   a diffuser in the housing body, acting as a one-way check-valve to diffuse the propellant upon its release from the propellant canister;
   a dose holding chamber in the housing body, separated from the propellant canister, capable of containing a unit dose of the compound, the dose holding chamber positioned such that the released propellant flows into the dose holding chamber from the diffuser and causes the compound to be propelled from the dose holding chamber;
   a nozzle positioned such that the compound flows through the nozzle upon being propelled from the dose holding chamber for delivery to the nasal cavity; and
   an actuation element comprising an actuation lever, wherein actuation of the actuation lever is configured to displace the propellant canister from the unactuated position to the actuated position.

2. The device of claim 1, wherein the actuation lever is an L-shaped lever arm, wherein a first member of the actuation lever is positioned to receive a contact force from an actuation button and a second member of the actuation lever perpendicular to the first member applies a contact force to the propellant canister upon actuation of the actuation button.

3. The device of claim 1, wherein the actuation element comprises an actuation button exposed from the housing body, wherein depression of the actuation button in a direction towards the housing body drives the propellant canister into the puncture element, thereby puncturing the propellant canister.

4. The device of claim 1, wherein the device further comprises a removeable cap configured to maintain the actuation element in an unactuated position.

5. The device of claim 1, further comprising a lock configured to maintain the actuation element in an actuated position.

6. The device of claim 1, further comprising a use indicator configured to provide an indication that the actuation element is in an actuated position.

7. The device of claim 1, wherein the actuation element contains a sliding element exposed from the housing body, wherein the sliding element is slideable between an unactuated position that enables positioning of the propellant canister in the unactuated position and an actuated position that forces the propellant canister to the actuated position.

8. A device for delivery of a compound to a nasal cavity, the device comprising:
   a propellant canister in a housing body capable of containing a propellant which is different from the compound, the propellant canister displaceable between an unactuated position and an actuated position;
   a dose holding chamber, separated from the propellant canister, capable of containing a unit dose of the compound; a nozzle positioned such that the compound flows through the nozzle upon being propelled from the dose holding chamber by the propellant for delivery to the nasal cavity;
   an actuation element comprising an actuation lever, wherein actuation of the actuation lever is configured to displace the propellant canister from the unactuated position to the actuated position;
   and a puncture element positioned to puncture a propellant canister position and cause release of the propellant from the propellant canister when the propellant canister is displaced to the actuated position.

9. The device of claim 8, wherein the actuation lever is an L-shaped lever arm, wherein a first member of the actuation lever is positioned to receive a contact force from an actuation button and a second member of the actuation lever perpendicular to the first member applies a contact force to the propellant canister upon actuation of the actuation button.

10. The device of claim 8, wherein the actuation element comprises an actuation button exposed from the housing body, wherein depression of the actuation button in a direction towards the housing body drives the propellant canister into the puncture element, thereby puncturing the propellant canister.

11. The device of claim 8, wherein the device further comprises a removeable cap configured to maintain the actuation element in an unactuated position.

12. The device of claim 8, further comprising a lock configured to maintain the actuation element in an actuated position.

13. The device of claim 8, further comprising a use indicator configured to provide an indication that the actuation element is in an actuated position.

14. The device of claim 8, wherein the actuation element contains a sliding element exposed from the housing body, wherein the sliding element is slideable between an unactuated position that enables positioning of the propellant canister in the unactuated position and an actuated position that forces the propellant canister to the actuated position.

15. A device for delivery of a compound to a nasal cavity, the device comprising:
a housing body;
a propellant canister in the housing body containing a propellant which is different from the compound, the propellant canister displaceable between an unactuated position and an actuated position;
a puncture element in the housing body positioned to puncture the propellant canister position and cause release of the propellant from the propellant canister;
a diffuser in the housing body, acting as a one-way check-valve to diffuse the propellant upon its release from the propellant canister;
a dose holding chamber in the housing body, separated from the propellant canister, containing the compound, the dose holding chamber positioned such that the propellant flows into the dose holding chamber from the diffuser and causes the compound to be propelled from the dose holding chamber;
a nozzle positioned such that the released compound flows through the nozzle upon being propelled from the dose holding chamber for delivery to the nasal cavity; and
an actuation element comprising an actuation lever, wherein actuation of the actuation lever is configured to displace the propellant canister from the unactuated position to the actuated position.

16. The device of claim 15, wherein the actuation lever is an L-shaped lever arm, wherein a first member of the actuation lever is positioned to receive a contact force from an actuation button and a second member of an actuation level perpendicular to the first member applies a contact force to the propellant canister upon actuation of the actuation button.

17. The device of claim 15, wherein the actuation element comprises an actuation button exposed from the housing body, wherein depression of the actuation button in a direction towards the housing body drives the propellant canister into the puncture element, thereby puncturing the propellant canister.

18. The device of claim 15, wherein the actuation element contains a sliding element exposed from the housing body, wherein the sliding element is slideable between an unactuated position that enables positioning of the propellant canister in the unactuated position and an actuated position that forces the propellant canister to the actuated position.

19. The device of claim 15, wherein the device further comprises a removeable cap configured to maintain the actuation element in an unactuated position.

20. The device of claim 15, further comprising a lock configured to maintain the actuation element in an actuated position.

* * * * *